United States Patent [19]

Woznicki et al.

[11] Patent Number: 4,802,924

[45] Date of Patent: Feb. 7, 1989

[54] COATINGS BASED ON POLYDEXTROSE FOR AQUEOUS FILM COATING OF PHARMACEUTICAL FOOD AND CONFECTIONARY PRODUCTS

[75] Inventors: Edward J. Woznicki, Douglassville; Susan M. Grillo, Telford, both of Pa.

[73] Assignee: Colorcon, Inc., West Point, Pa.

[21] Appl. No.: 876,186

[22] Filed: Jun. 19, 1986

[51] Int. Cl.$^4$ .............................................. A61K 9/00
[52] U.S. Cl. ........................................ 427/3; 424/479; 424/480
[58] Field of Search ............... 424/479, 480, 440; 427/3; 426/302; 106/213, 214

[56] References Cited

U.S. PATENT DOCUMENTS

| | | | |
|---|---|---|---|
| 2,531,536 | 11/1950 | Silver | 426/103 |
| 2,563,014 | 8/1951 | Durand | 127/34 |
| 3,421,920 | 1/1967 | Theth et al. | 106/217 |
| 3,766,165 | 10/1973 | Rennhard | 260/209 R |
| 3,868,465 | 2/1975 | Furda et al. | 426/576 |
| 3,876,794 | 4/1975 | Rennhard | 426/548 |
| 3,981,984 | 9/1976 | Signorino | 424/480 |
| 4,302,440 | 11/1931 | John et al. | 424/35 |
| 4,382,963 | 5/1983 | Klose et al. | 426/3.00 |
| 4,528,206 | 7/1985 | Kastin | 426/660 |
| 4,543,370 | 9/1985 | Porter et al. | 523/100 |
| 4,572,838 | 2/1986 | Lanier et al. | 426/643 |
| 4,610,891 | 9/1986 | Miyamoto et al. | 424/479 |

OTHER PUBLICATIONS

Rowe "Molecular Weight Studies on Hydroxypropyl Methylcellulose Phthalate (HP 55)" Acta-Pharm Technologica 28 (2), p. 129, 1982.

Osterwald "Properties of Film-Formers and Their Use in Aqueous Systems" Pharmaceutical Research 1985, p. 15.

Primary Examiner—Edward J. Smith
Assistant Examiner—Peter F. Kulkosky
Attorney, Agent, or Firm—John F. A. Earley; John F. A. Earley, III

[57] ABSTRACT

Providing a film coating on pharmaceutical tablets, foods, confectionery forms and the like by coating them with polydextrose, or a combination of polydextrose and cellulosic polymer, or a layer of polydextrose overcoated by a layer of cellulosic polymer.

32 Claims, No Drawings

COATINGS BASED ON POLYDEXTROSE FOR AQUEOUS FILM COATING OF PHARMACEUTICAL FOOD AND CONFECTIONARY PRODUCTS

TECHNICAL FIELD

This invention is in the field of aqueous film coating of pharmaceutical, food and confectionery products, and is more specifically concerned with providing such coatings based on polydextrose.

BACKGROUND OF THE INVENTION

Cellulose polymers such as hydroxypropyl methylcellulose have long been recognized in the art as being suitable for the aqueous film coating of pharmaceutical tablets and the like.

While it is normally possible to produce excellent film coatings with such cellulosic materials, difficulties can sometimes arise with respect to the ability of the resultant film coatings to adhere satisfactorily to the surface to which they are applied. This is especially true when considering tablet substrates such as waxy matrix sustained release products and multivitamin products (with which the phenomenon of "bridging" of the coating across debossed legends can be a substantial problem).

It is also desirable to be able to produce film coatings for food and confectionery products which are able to replace the currently used sugar coatings, in order to meet the requirements for low calorie, noncariogenic (that is, not harmful to teeth) coatings for such products.

While cellulosic polymers can meet these requirements, they tend to produce coatings that have undesirable taste and mouth-feel (that is, they are somewhat bitter and slimy in texture; both undesirable features especially for confectionery products).

SUMMARY OF THE INVENTION

Aqueous film coatings based on the polymer polydextrose provide the solution to both the pharmaceutical, and the food and confectionery problems described. Used alone, or in combination with other polymers, polydextrose produces pharmaceutical film coatings that exhibit excellent adhesive qualities, while when used in food and confectionery applications, it can produce coatings with good organoleptic properties that are low calorie and non-cariogenic in nature.

One characteristic of polydextrose, however, is that it has an extremely low average molecular weight value (for example, peak molecular weight, $M_p$, is approximately 1230). It is well known that low molecular weight polymers produce extremely weak films. Rowe ("Molecular Weight Studies on Hydroxypropyl Methylcellulose Phthalate" *Acta-Pharm. Technologica* 28 (2), p. 129 1982) has stated that for the purposes of film coating, there exists a CRITICAL MOLECULAR WEIGHT value for polymers such as hydroxypropyl methylcellulose (H.P.M.C.), below which there is a great risk of the coating cracking. For H.P.M.C., he stated that the $M_p$ value, which is indicative of the molecular weight of the main component, is approximately $8.0 \times 10^4$.

This value for HPMC is significantly greater than the $M_p$ value for polydextrose, which would thus not be expected to produce satisfactory film coatings.

Additionally, Osterwald ("Properties of Film-Formers and Their Use in Aqueous Systems", *Pharm. Res.*, 1985, p. 15) has stated that for film coating, polymers producing solutions (containing 2% w/w of the polymer in water) having viscosities in the range of 3-15 mPas (milli Pascal seconds) (same as centipoise numerically) ought to be used, and that below this range, the polymer chains shorten to such an extent that the stability of the film is affected (i.e. film strength decreases too much). Two percent aqueous solutions of polydextrose have a viscosity of less than 2 mPas (in fact the value is too low to be differentiated from that of plain water).

Consequently, to those skilled in the art, polydextrose would be considered to produce film coatings that are entirely unsuitable for modern film coating processes; yet we have found it can produce excellent film coatings that in some cases have superior properties to those obtained from more traditional polymers.

Finally, polydextrose can be formulated into a dry-edible film coating composition, shipped to the user and mixed easily into water to form an aqueous coating suspension.

The aqueous coating suspension comprises an effective amount of polydextrose, plasticizer, detackifier, and a secondary film former, mixed into water to form an aqueous coating suspension which may be applied to the forms to be coated, as by spraying. Optionally, a colorant may be added to the aqueous coating suspension before the coating step. Also, a cellulosic polymer, such as hydroxypropyl methylcellulose, may be substituted for the secondary film former, and the resulting formula is particularly adapted for coating waxy matrix tablets, which are particularly difficult to coat.

The film former of the coating is polydextrose, or a mixture of polydextrose and a cellulosic polymer film former. Also, it may be advantageous to coat with a layer of polydextrose aqueous coating suspension, and then overcoat with a layer of cellulosic film polymer coating suspension.

The cellulosic film polymer may be hydroxypropyl methylcellulose or hydroxypropyl cellulose.

The plasticizer may be polyethylene glycol, triacetin, propylene glycol, or acetyltriethyl citrate.

The colorants may be FD&C lakes, D&C lakes, titanium dioxide, or dyes approved for ingestion by the U.S. Federal Drug Administration. Examples of such pigments are listed in Colorcon U.S. Pat. No. 4,543,370 issued Sept. 24, 1985, and incorporated herein by reference.

The detackifier may be lecithin or mineral oil.

The secondary film former may be sodium alginate or propylene glycol alginate.

The polydextrose coating is especially effective in coating tablets and the like having debossed or intaglio logos, trademarks, designs or words thereon since it adheres to the tablet surfaces without bridging and obscuring the debossed or intaglio printing.

DETAILED DESCRIPTION

We now turn to the examples of the invention, all of which disclose formulations which may be mixed into water to form an aqueous coating suspension that may be effective to coat pharmaceuticals, food, and confectioneries.

This invention is concerned with coating pharmaceutical, confectionery and food forms including medicinal tablets, vitamin tablets, aspirin tablets, capsules, chewing gum balls, chocolates, pieces of candy, almonds, breakfast cereal, and the like.

EXAMPLES

The following examples illustrate the invention. All units and percentages used herein are by weight.

Example 1

A clear coating suspension is made for coating chocolates by mixing the following ingredients into water to form an aqueous coating solution.

|  | % | Grams |
|---|---|---|
| Polydextrose | 81.42 | 2050 |
| Soda Ash | 0.72 | 18.2 |
| Kelgin LV | 4.96 | 125 |
| Alcolec F-100 | 2.98 | 75 |
| Triacetin | 4.96 | 125 |
| PEG 8000 | 4.96 | 125 |

Polydextrose is made by Pfizer, Inc., Kelgin LV is sodium alginate made by the Kelco division of Merck and is used as a secondary film former, Alcolec F-100 is water miscible lecithin made by the American Lecithin Co. and is used as a detackifier in the formula, triacetin is triethyl citrate by Pfizer and is used as a plasticizer and PEG 8000 is polyethylene glycol 8000 and is used in the formula as a plasticizer.

The mixing procedure is to mix 300 grams of the dry ingredients into about 1700 milliliters of water to make an aqueous coating.

The chocolates to be coated are placed in a 24 inch Accela Cota coating pan with 4 anti-skid bars, and the aqueous coating suspension is sprayed onto the chocolates. During the coating procedure, the inlet air is 45° C., the outlet air is 30° C., the atomizing air is 3 bar, the pan speed is 12 rpm, the feed rate is 18 grams/minute, and the coating time is 90 minutes. The procedure produced a very nice coating on the chocolates with no tack, and with no slimy taste.

Example 2

In order to coat vitamin tablets, a formula having the following ingredients is dry mixed together and then mixed into water to form an aqueous coating suspension which is sprayed onto the vitamin tablets:

|  | % | Grams |
|---|---|---|
| Polydextrose | 68.38 | 492.3 |
| Kelgin LV | 4.18 | 30.1 |
| Alcolec F-100 | 2.51 | 18.1 |
| Triacetin | 2.09 | 15.0 |
| PEG 8000 | 6.27 | 45.1 |
| R-40 lake | 12.50 | 90.0 |
| TiO$_2$ | 4.00 | 28.8 |
|  |  | 720.0 |
| H$_2$O |  | 4080.0 |
|  |  | 4800.0 |

The R-40 lake is FD&C Red number 40 aluminum lake made by Colorcon, Inc., West Point, Pa.

The mixing procedure is to blend all dry ingredients into a blender for about 5 minutes, and add triacetin and blend for an additional 5 minutes. Then the formula is mixed into 4080 milliliters of distilled water to form an aqueous coating solution.

A 24 inch Accela Cota coating pan is loaded with 11 kilograms of vitamin tablets which have a debossed or intaglio logo on them. The spray coating parameters are inlet air 85° C., outlet air 50° C., atomizing air 3 bar, pan speed 12 rpm, feed rate 60 grams/minute, and coating time 80 minutes. The vitamin tablets receive a very nice coating with a good logo with no bridging, and no tack.

Example 3

It is desired to color gumballs and for this purpose the following formula is dry mixed together and is mixed into water to make an aqueous coating suspension which is sprayed onto the gumballs.

|  | % | Grams |
|---|---|---|
| Polydextrose | 70.0 | 210.0 |
| PEG 400 | 2.5 | 7.5 |
| Sodium Alginate MV | 5.0 | 15.0 |
| TiO$_2$ | 10.0 | 30.0 |
| Alcolec F-100 | 2.5 | 7.5 |
| Y-5 HT lake | 10.0 | 30.0 |

The Y-5 HT lake is FD&C Yellow number 5 aluminum lake made by Colorcon, Inc., West Point, Pa. The solids of this aqueous coating suspension amount to 300 grams and the water amounts to 1700 grams, so the suspension is about 15% solids. In spray coating the gumballs, the inlet air is 66° C., the outlet air is 35° C., the atomizing air is 3 bar, the feed rate is 30 grams/minute, the pan speed is 18 rpm, and the coating time is 45 minutes.

Example 4

Instead of coating the gumballs with a lake formula as in Example 3, it is desired to coat the gumballs with a dye formula, and the following formula is mixed into water to form an aqueous coating suspension which is sprayed onto the gumballs.

|  | % | Grams |
|---|---|---|
| Polydextrose | 79.5 | 238.5 |
| PEG 400 | 2.5 | 7.5 |
| Sodium Alginate MV | 5.0 | 15.0 |
| TiO$_2$ | 10.0 | 30.0 |
| Alcolec F-100 | 2.5 | 7.5 |
| Y-5 Dye | 0.5 | 1.5 |

The Y-5 dye is FD&C Yellow number 5 dye approved by the U.S. Federal Drug Administration for ingestion, the solids content amounts 300 grams, and the water content of the aqueous coating suspension is 1700 grams, the suspension being about 15% solids. The air, feed rate, and pan speed parameters of the spraying are the same as in Example 3 except the coating time is 50 minutes.

Example 5

It is desired to coat almonds with a cherry color, and the following formula is mixed together and into an aqueous suspension and sprayed onto the almonds.

|  | % | Grams |
|---|---|---|
| Polydextrose | 68.47 | 1711.75 |
| Sodium Alginate (Kelgin LV) | 4.18 | 104.50 |
| Alcolec F-100 | 2.51 | 62.75 |
| Triacetin | 4.18 | 104.50 |
| PEG 8000 | 4.18 | 104.50 |
| R-40 HT lake | 13.39 | 334.75 |
| Y-6 HT lake | 3.11 | 77.75 |

The sodium alginate is a secondary film former that gives the resulting coating a glossy appearance. The R-40 HT lake is FD&C Red number 40 aluminum lake, and the Y-6 HT lake is FD&C Yellow number 6 aluminum lake, both made and sold by Colorcon, Inc. West Point, Pa. The formula, 240 grams, is mixed into 960 milliliters of water, and the resulting aqueous coating suspension is spray coated onto the almonds in a coating pan. The almonds may have previously been given a subcoat of the clear polydextrose formula of Example 1, by spraying the Example 1 aqueous coating suspension onto the almonds with inlet air 73° C., outlet air 48° C., atomizing air 45 psi, pan speed 12 rpm, feed rate 34 grams/minute, and coating time 35 minutes.

To apply the cherry color to the almonds, the almonds are placed in a coating pan and the cherry color aqueous coating suspension is sprayed onto the almonds as they are being rotated in the pan, with the inlet air being 73° C., the outlet air being 48° C., the atomizing air being 45 psi. the pan speed being 12 rpm, and the feed rate being 40 grams/minute, and the coating time being 30 minutes.

Example 6

It is desired to coat KIX breakfast cereal with polydextrose, and the following formula is mixed into an aqueous suspension which is sprayed onto the KIX cereal puffs in a fluidized bed coater, such as made by Aeromatic.

|  | % | Grams |
|---|---|---|
| Polydextrose | 71.00 | 16.05 |
| PEG 400 | 2.26 | 0.51 |
| Kelgin LV | 4.52 | 1.02 |
| Alcolec F-100 | 2.26 | 0.51 |
| TiO$_2$ | 10.00 | 2.26 |
| Y-5 HT lake | 10.00 | 2.26 |
|  |  | 22.60 |
| H$_2$O |  | 277.5 |

The procedure is to partly fill the bed coater cone with KIX cereal puffs, and turn on the coater to support the puffs in the air, and spray the puffs with the aqueous suspension. The inlet temperature is 80° C., the outlet temperature is 38° C., the feed rate is 10 grams/minute, and the air is 1 bar.

Example 7

Polydextrose may be combined with a cellulosic polymer, such as Methocel E5, to obtain the superior adhesiveness of the polydextrose and the superior mositure barrier of the cellulosic polymer in coating vitamin tablets. An example of a formula is as follows.

|  | % | Grams |
|---|---|---|
| Polydextrose | 34.24 | 246.5 |
| Methocel E5 | 34.24 | 246.5 |
| Kelgin LV | 4.18 | 30.1 |
| Alcolec F-100 | 2.51 | 18.1 |
| Triacetin | 2.09 | 15.0 |
| PEG 8000 | 6.27 | 45.1 |
| Y-5 HT lake | 12.50 | 90.0 |
| TiO$_2$ | 4.00 | 28.8 |

The Y-5 HT lake is FD&C Yellow number 5 lake made by Colorcon, Inc., West Point, Pa. The formula contains 720 grams of solids and is mixed into 4080 milliliters of water to give a total weight of the aqueous coating suspension of 4800 grams. Methocel E-5 is hydroxypropyl methyl cellulose made by Dow Chemical Co. The aqueous coating suspension is sprayed onto tablets in a coating pan with inlet air at 85° C., outlet air at 50° C., atomizing air 3 bar, pan speed 12 rpm, feed rate 53 grams/minute, and coating time 90 minutes.

Example 8

Another example of a formula paraticularly adapted for applying a coating to vitamin tablets with intaglio logos without bridges comprises a 75% to 25% ratio of polydextrose to Methocel E-5, instead of the 50% to 50% ratio shown in Example 7, and is listed below.

|  | % | Grams |
|---|---|---|
| Polydextrose | 51.36 | 369.8 |
| Methocel E-5 | 17.12 | 123.3 |
| Kelgin LV | 4.18 | 30.1 |
| Alcolec F-100 | 2.51 | 18.1 |
| Triacetin | 2.09 | 15.0 |
| PEG 8000 | 6.27 | 45.1 |
| Y-6 HT lake | 12.50 | 90.0 |
| TiO$_2$ | 4.00 | 28.8 |

Example 9

Another example of a formula containing a mixture of polydextrose and a cellulosic polymer for coating vitamin tablets is:

|  | % | Grams |
|---|---|---|
| Polydextrose | 51.36 | 369.8 |
| Klucel EF | 17.12 | 123.3 |
| Kelgin LV | 4.18 | 30.1 |
| Alcolec F-100 | 2.51 | 18.1 |
| Triacetin | 2.09 | 15.0 |
| PEG 8000 | 6.27 | 45.1 |
| Y-6 HT lake | 12.50 | 90.0 |
| TiO$_2$ | 4.00 | 28.8 |

Klucel EF is hydroxypropyl cellulose by Hercules, Inc.

Example 10

Another example of a formula containing both polydextrose and a cellulosic polymer is as follows.

|  | % | Grams |
|---|---|---|
| Polydextrose | 61.60 | 443.50 |
| Klucel EF | 6.80 | 48.96 |
| Kelgin LV | 4.18 | 30.10 |
| Alcolec F-100 | 2.51 | 18.10 |
| Triacetin | 2.09 | 15.00 |
| PEG 8000 | 6.26 | 45.10 |
| R-40 HT lake | 6.25 | 45.00 |
| Y-6 HT lake | 6.25 | 45.00 |
| TiO$_2$ | 4.06 | 29.23 |

Example 11

Another formula containing a mixture of polydextrose and hydroxypropyl methyl cellulose is as follows.

|  | % | Grams |
|---|---|---|
| Polydextrose | 36.86 | 921.5 |
| Methocel E-5 | 36.86 | 921.5 |
| Kelgin LV | 4.50 | 112.5 |
| Alcolec F-100 | 2.70 | 67.5 |
| Triacetin | 2.25 | 56.3 |

-continued

| | % | Grams |
|---|---|---|
| PEG 8000 | 6.75 | 168.8 |
| TiO2 | 9.32 | 233.0 |
| B-1 lake | 0.76 | 19.0 |

The B-1 lake is FD&C Blue number 1 aluminum lake.

This formula is especially advantageous if it is desired to coat waxy matrix tablets, such as Dimetaps by A. H. Robbins, which are very hard to coat because it is difficult to get anything to adhere to their waxy surface.

The formula ingredients are mixed into sufficient water to make 15% solids suspension, and the suspension is sprayed onto waxy matrix tablets at 45° C. inlet air, 30° C. outlet air, 3 bar atomizing air, 44 grams/minute feed rate, and 12 rpm pan speed.

Example 12

The outer surface of gumballs may be very rough with a large number of holes, and it may be desirable to apply a subcoat and fill in the holes before applying the thin coating of polydextrose as in Example 1, for example. A suitable subcoat may be made from the following formula into an aqueous coating suspension and sprayed onto the gumballs.

| | % | Grams |
|---|---|---|
| Polydextrose | 52.2 | 208.8 |
| PEG 400 | 1.8 | 7.2 |
| Sodium Alginate | 7.0 | 28.0 |
| Titanium Dioxide | 7.0 | 28.0 |
| Alcolec F-100 | 2.1 | 8.4 |
| Avicel 105 microcrystalline cellulose | 30.0 | 120.0 |

PEG 400 is polyethylene glycol 400.

Example 13

Another formula for coating chocolates, an orange color, is as follows.

| | % | Grams |
|---|---|---|
| Polydextrose | 68.81 | 206.4 |
| Kelgin LV | 4.18 | 12.5 |
| Alcolec F-100 | 2.15 | 6.5 |
| Triacetin | 4.18 | 12.5 |
| PEG 8000 | 4.18 | 12.5 |
| Red 40 lake | 13.39 | 40.2 |
| Y-6 lake | 3.11 | 9.3 |

Example 14

Vitamin tablets are spray coated in a coating pan with an aqueous coating suspension of Example 1 with the inlet air 85° C., outlet air 50° C., atomizing air 3 bar, pan speed 12 rpm, feed rate 60 grams/minute, and coating time 80 minutes.

Then the polydextrose coated vitamin tablets are spray coated with an OPADRY coating suspension made in accordance with the disclosure in Colorcan, Inc. U.S. Pat. No. 4,543,370 which issued Sept. 24, 1985, which is incorporated herein by reference.

ADVANTAGES

The polydextrose coatings of the invention have the advantage of adhering to surfaces that are difficult to coat, such as the waxy matrix surfaces of some pharmaceutical tablets, such as Dimetaps. The coatings also have the further advantage of adhering to the debossed or intaglio surfaces of logos or words on tablets without obscuring those logos or words. This is very important when a manufacturer debosses his trademark, which may be a design or words, on his product, Previously, coatings made of cellulosic polymer film formers would bridge the grooves formed by the debossed word or design on the tablet, and would obscure it so that it could not be read.

In addition to coating waxy matrix tablets, the polydextrose coating of the invention is particularly adapted to coat sugarless chewing gum pieces which are very difficult to coat in an aqueous system. The coating suspension of Example 3 is particularly effective in coating sorbitol gum pieces.

We claim:

1. A method of film coating pharmaceutical tablets, food, confectionery forms and the like with a protective film coating comprising the steps of
   mixing polydextrose, plasticizer, detackifier, and secondary film former into water to form an aqueous coating suspension,
   spraying an effective amount of said coating suspension onto said tablets to form a film coating on said tablets,
   and drying the film coating on said tablets,
   wherein the amount of polydextrose used is sufficient to yield improved results as compared to a similar coating absent polydextrose.

2. The method of claim 1, including
   dispersing a colorant in the coating suspension before applying the coating suspension to the tablets.

3. The method of claim 1, wherein
   the plasticizer is polyethylene glycol, triacetin, propylene glycol, or acetyltriethyl citrate.

4. The method of claim 1, wherein
   the plasticizer is in a range of 2.5% to 10% by weight of the non-water ingredients of the aqueous coating suspension.

5. The method of claim 1, wherein
   the detackifier is lecithin or mineral oil.

6. The method of claim 1, wherein
   the detackifier is in the range of 1% to 3% by weight of the non-water ingredients of the aqueous coating suspension.

7. The method of claim 1, wherein
   the secondary film former is sodium alginate or propylene glycol alginate.

8. The method of claim 1, wherein
   the secondary film former is in the range of 2% to 10% by weight of the non-water ingredients of the aqueous coating suspension.

9. The method of claim 2, wherein
   said colorants are FD&C lakes, D&C lakes, titanium dioxide, or FD&C or D&C dyes.

10. The method of claim 2, wherein
    said colorants are in the range of 0% to 25% by weight of the non-water ingredients of the aqueous coating suspension.

11. The method of claim 1
    the plasticizer being polyethylene glycol, triacetin, propylene glycol, or acetyltriethyl citrate,
    the detackifier is lecithin or mineral oil,
    the secondary film former is sodium alginate or propylene glycol alginate,
    and the colorants are FD&C lakes, D&C lakes, titanium dioxide, or FD&C or D&C dyes.

12. The method of claim 1,
the polydextrose being 30 to 90% by weight of the non-water ingredients of the aqueous coating suspension,
dispersing a colorant in the coating suspension before applying the coating suspension to the tablets,
the colorants being FD&C lakes, D&C lakes, titanium dioxide, or FD&C or D&C dyes, and are 0 to 25% by weight of the non-water ingredients of the suspension,
the plasticizer being polyethylene glycol, triacetin, propylene glycol, or acetyltriethyl citrate in a range of 2.5% to 10% by weight of the non-water ingredients of the suspension,
the detackifier being lecithin or mineral oil in a range of 1 to 3% by weight of the non-water ingredients of the aqueous coating suspension,
the secondary film former being sodium alginate or propylene glycol alginate in a range of 2% to 10% by weight of the non-water ingredients of the aqueous coating suspension, and
wherein the amount of polydextrose used is sufficient to yield improved results as compared to a similar coating absent polydextrose.

13. A method of film coating pharmaceutical tablets, food, confectionery forms and the like with a protective film comprising the steps of
mixing polydextrose, plasticizer, detackifier, and secondary film former into water to form an aqueous coating suspension,
said tablets having debossed words or designs on their outer surface,
spraying an effective amount of said coating suspension onto said tablets to form a film coating thereon without obscuring the debossed words or designs by bridging, and
drying the film coating on said tablets,
wherein the amount of polydextrose used is sufficient to yield improved results as compared to a similar coating absent polydextrose.

14. A method of film coating pharmaceutical tablets, food, confectionery forms and the like with a protective film comprising the steps of
mixing polydextrose, plasticizer, and a cellulosic polymer into water to make an aqueous coating suspension,
spraying an effective amount of said coating suspension onto said tablets to form a film coating on said tablets,
and drying the film coating on said tablets,
wherein the amount of polydextrose used is sufficient to yield improved results as compared to a similar coating absent polydextrose.

15. The method of claim 14,
the cellulosic polymer being hydroxypropyl methyl cellulose or hydroxypropyl cellulose.

16. The method of claim 14, including
mixing a detackifier into said aqueous coating suspension.

17. The method of claim 14, including
dispersing a colorant in the coating suspension before applying the coating suspension onto the tablets.

18. The method of claim 14, wherein
the plasticizer is polyethylene glycol, triacetin, propylene glycol, or acetyltriethyl citrate, or a mixture thereof.

19. The method of claim 15, wherein
the plasticizer is in a range of 2.5% to 10% by weight of the aqueous coating suspension without the water.

20. The method of claim 16, including
the detackifier being lecithin or mineral oil.

21. The method of claim 16, wherein
the detackifier is in the range of 1% to 3% by weight of the non-water ingredients of the aqueous coating suspension.

22. The method of claim 17, wherein
said colorants are FD&C lakes, D&C lakes, titanium dioxide, or FD&C or D&C dyes.

23. The method of claim 17, wherein
said colorants are in the range of 0% to 26% by weight of the non-water ingredients of the aqueous coating suspension.

24. A method of film coating pharmaceutical tablets, food, confectionery forms and the like with a protective film comprising the steps of
mixing together polydextrose, plasticizer, detackifier, secondary film former, and water to form an aqueous coating suspension,
spraying an effective amount of said coating suspension onto said tablets to form a film coating on said tablets,
and drying the film coating on said tablets,
spraying an effective amount of a cellulosic coating solution onto the tablets to form a cellulosic film coating on the tablets which overcoats said film coating,
and drying the cellulosic film coating on said tablets,
wherein the amount of polydextrose used is sufficient to yield improved results as compared to a similar coating absent polydextrose.

25. The method of claim 24, including
dispersing colorant in the cellulosic coating solution before spraying it onto said tablets.

26. The product made in accordance with the method of claim 1.

27. The product made in accordance with the method of claim 11.

28. The product made in accordance with the method of claim 12.

29. The product made in accordance with the method of claim 13.

30. The product made in accordance with the method of claim 14.

31. The product made in accordance with the method of claim 24.

32. A method of coating pharmaceutical tablets, food, confectionery forms and the like with a protective film comprising the steps of
mixing a primary film-former comprising polydextrose and a cellulosic film former, with the polydextrose being in the range of 10 to 100% by weight of the primary film-former being in the range of 0 to 90% of, a plasticizer, a detackifier, and a secondary film-former into water to form an aqueous coating suspension,
spraying an effective amount of said coating suspension onto said tablets to form a film coating on said tablets,
and drying the film coating on said tablets wherein the amount of polydextrose used is sufficient to yield improved results as compared to a similar coating absent polydextrose.

* * * * *